(12) United States Patent
Kosonen et al.

(10) Patent No.: US 9,792,787 B2
(45) Date of Patent: *Oct. 17, 2017

(54) WEARABLE ELECTRONIC DEVICE

(71) Applicant: Nokia Technologies Oy, Espoo (FI)

(72) Inventors: Matti Kosonen, Jarvenpaa (FI); Sami Myyrylainen, Espoo (FI)

(73) Assignee: Nokia Technologies Oy, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/083,766

(22) Filed: Mar. 29, 2016

(65) Prior Publication Data

US 2016/0210826 A1 Jul. 21, 2016

Related U.S. Application Data

(63) Continuation of application No. 14/039,043, filed on Sep. 27, 2013, now Pat. No. 9,311,792.

(51) Int. Cl.
| | |
|---|---|
| *H04B 3/36* | (2006.01) |
| *G08B 6/00* | (2006.01) |
| *H04M 3/02* | (2006.01) |
| *H04M 3/42* | (2006.01) |
| *A61B 5/021* | (2006.01) |
| *A61B 5/00* | (2006.01) |
| *A61B 5/024* | (2006.01) |
| *H04M 1/725* | (2006.01) |

(52) U.S. Cl.
CPC ............... *G08B 6/00* (2013.01); *A61B 5/021* (2013.01); *A61B 5/024* (2013.01); *A61B 5/6843* (2013.01); *H04M 3/02* (2013.01); *H04M 3/42136* (2013.01); *H04M 1/7253* (2013.01); *H04M 2250/12* (2013.01)

(58) Field of Classification Search
CPC .. G08B 6/00; H04M 3/42136; H04M 2250/12
USPC ..... 340/407.1, 407.3, 539.11, 686.1, 870.02, 340/870.03
See application file for complete search history.

(56) References Cited

U.S. PATENT DOCUMENTS

| | | |
|---|---|---|
| 5,979,456 A | 11/1999 | Magovern |
| 8,344,862 B1 | 1/2013 | Donham |
| 9,024,749 B2 | 5/2015 | Ratajczyk |

(Continued)

FOREIGN PATENT DOCUMENTS

| | | |
|---|---|---|
| CN | 102831760 | 12/2012 |
| JP | 03-141925 | 6/1991 |

(Continued)

OTHER PUBLICATIONS

International Search Report for International Application No. PCT/FI2014/050605, Date of Completion of Search: Oct. 15, 2014, 5 pages.
PCT Written Opinion of the International Searching Authority for International Application No. PCT/FI2014/050605, Date of Completion of Opinion: Oct. 15, 2014, 8 pages.

(Continued)

*Primary Examiner* — Tai T Nguyen
(74) *Attorney, Agent, or Firm* — Locke Lord LLP

(57) ABSTRACT

An apparatus including an elongated apparatus structure configured to fit around a body part of a user and an actuator configured to change shape of the elongated apparatus structure. The actuator is configured to change tightness of the elongated apparatus structure around the body part of the user based on an action the apparatus is performing.

24 Claims, 4 Drawing Sheets

(56) References Cited

U.S. PATENT DOCUMENTS

| | | |
|---|---|---|
| 9,365,387 B2 | 6/2016 | Beers et al. |
| 2003/0083593 A1 | 5/2003 | Marmaropoulos et al. |
| 2003/0181116 A1 | 9/2003 | Van Heerden et al. |
| 2004/0210165 A1 | 10/2004 | Marmaropoulos et al. |
| 2006/0115348 A1 | 6/2006 | Kramer |
| 2006/0169989 A1 | 8/2006 | Bhattacharya et al. |
| 2007/0026798 A1 | 2/2007 | Hoogstra |
| 2007/0106457 A1 | 5/2007 | Rosenberg |
| 2008/0058620 A1 | 3/2008 | Lee et al. |
| 2008/0114538 A1 | 5/2008 | Lindroos |
| 2008/0291225 A1 | 11/2008 | Arneson |
| 2010/0164888 A1 | 7/2010 | Okumura et al. |
| 2011/0043496 A1 | 2/2011 | Avalani |
| 2011/0270435 A1* | 11/2011 | Hyde .................. A61B 5/1077 700/132 |
| 2013/0131887 A1 | 5/2013 | Park |
| 2013/0154826 A1 | 6/2013 | Ratajczyk |

FOREIGN PATENT DOCUMENTS

| | | |
|---|---|---|
| JP | 2004-147263 | 5/2004 |
| JP | 2008-062065 | 3/2008 |
| JP | 2008-168054 | 7/2008 |
| WO | WO2008087870 | 7/2008 |
| WO | WO2012004752 | 1/2012 |

OTHER PUBLICATIONS

Koo, I.M. et al., "Development of Soft-Actuator-Based Wearable tactile Display", IEEE Transactions on Robotics, vol. 24, No. 3, Jun. 2008, pp. 549-558.

English Language Machine Translation of Abstract to Japanese Patent Application Publication No. JP03-141925, dated Jun. 17, 1991, 1 page.

English Language Machine Translation of Japanese Patent Application Publication No. JP2008-168054, dated Jul. 24, 2008, 9 pages.

English Language Machine Translation of Japanese Patent Application Publication No. JP2008-062065, dated Mar. 21, 2008, 15 pages.

English Language Machine Translation of Chinese Patent Application Publication No. CN102831760 published on Dec. 19, 2012, 14 pages.

Search Report of Chinese Office Action dated Feb. 20, 2017 for Chinese Patent Application No. 201480061154, 2 pages.

Office Action dated Mar. 1, 2017 for Chinese Patent Application No. 201480061154, 8 pages.

English Language Machine Translation of Japanese Patent Application Publication No. JP2004-147263, published on May 20, 2004, 9 pages.

English Language Machine Translation of International Patent Application Publication No. WO2008087870, published on Jul. 24, 2008, 46 pages.

Extended European Search Report for EP Patent Application No. 14850070.5, dated Jun. 8, 2017, 9 pages.

* cited by examiner

WEARABLE ELECTRONIC DEVICE

INVENTION DISCLOSURE

The present U.S. Patent Application is a continuation of U.S. patent application Ser. No. 14/039,043, filed on Sep. 27, 2013, entitled "Wearable Electronic Device", now U.S. Pat. No. 9,311,792, and claims priority under 35 U.S.C. §120. The disclosure of the above priority application is incorporated herein, in its entirety, by reference.

TECHNICAL FIELD

The present invention generally relates to wearable electronic devices.

BACKGROUND ART

Electronic devices can be made of elastic, flexible or bendable material thereby enabling production of wearable electronic devices such as a wrist band or a chest band.

SUMMARY

According to a first example aspect of the invention there is provided an apparatus comprising
an elongated apparatus structure configured to fit around a body part of a user;
an actuator configured to change shape of the elongated apparatus structure;
wherein the actuator is configured to change tightness of the elongated apparatus structure around the body part of the user based on an action the apparatus is performing.

According to a second example aspect of the invention there is provided a method comprising
controlling an apparatus comprising an elongated apparatus structure configured to fit around a body part of a user and an actuator configured to change shape of the elongated apparatus structure; and
controlling the actuator to change tightness of the elongated apparatus structure around the body part of the user based on an action the apparatus is performing.

In an example implementation there is provided a computer program product comprising computer code for causing performing the method of any example aspect of the invention, when executed by an apparatus.

In an example implementation there is provided a non-transitory memory medium comprising computer code for causing performing the method of any example aspect of the invention, when executed by an apparatus.

Different non-binding example aspects and embodiments of the present invention have been illustrated in the foregoing. The above embodiments are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

The invention will be described, by way of example only, with reference to the accompanying drawings, in which.

DETAILED DESCRIPTION

Figure 1:
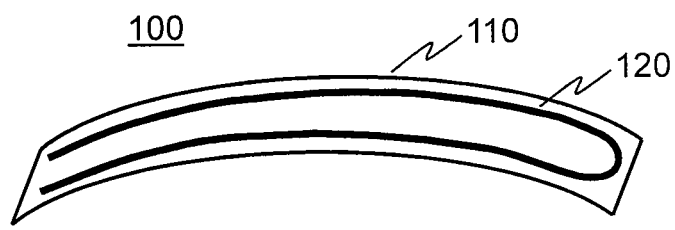
FIG. 1 shows a schematic view of an apparatus according to an example embodiment of the invention.

Some example embodiments of the present invention and potential advantages are understood by referring to FIGS. 1 through 9 of the drawings.

According to an example embodiment there is provided shaping and/or tightening of a wearable device with an actuator. The wearable device is for example a wrist band, a chest band, an ankle band or some other device comprising an elongated apparatus structure (e.g. a strap or a band) configured to fit around a body part or body extension of a user. The elongated apparatus structure is made of a suitable elastic, stretchable, flexible or bendable material (such as plastic, textile, or sheet metal), for example. Alternatively the elongated apparatus structure can be made of several strict or tough non-bendable parts (made of plastic, metal, or glass for example) that are linked to each other with a mechanical hinge or flexible/stretchable material to form the elongated structure. The actuator can be used for example for bending the elongated apparatus structure into a circular, oval, elliptical or the like form suited for being fitted around a body part or body extension of a user. It is to be noted that there may be one actuator or a plurality of actuators.

In an embodiment the actuator is configured to change tightness of the elongated apparatus structure around the body part of the user based on an action that is being performed by the wearable device or by a physically separate device or apparatus part that communicates with the wearable device over a communication connection. In an example, the shape of the elongated apparatus structure is changed automatically without specific user input or user action.

In an example embodiment the actuator is configured to change the shape of the elongated apparatus structure linearly so that any shape is available. In an alternative the actuator is configured to provide a stepwise shape change so that for example three different shapes or positions are provided. In an example embodiment there are an unbent position and two bent positions. In an example embodiment there are an unbent position, a loose fitting position and a tight fitting position. These examples are discussed in more detail in connection with FIGS. 1-4.

The method that is used for controlling the actuator depends on what type actuator is used. In an embodiment an actuator made of a shape memory alloy is used. In this case the shape change can be linear. The shape change is provided by changing current or voltage used for controlling the actuator and the shape depends on the current or voltage level. Alternatively there may be a locking mechanism that locks the apparatus structure to desired shape/shapes. In this solution power needs to be used only for driving the apparatus structure to the desired shape and thereafter the locking mechanism maintains the shape and power to the actuator can be switched off thereby saving energy.

In an alternative solution, the actuator can comprise a motor or a linear motor with appropriate mechanisms. In that case the shape change can be linear or stepwise without significant effect on power consumption.

In an example embodiment, the elongated apparatus structure is part of a wearable garment, such as a glove, sock, shirt or jacket.

FIG. 1 shows a schematic view of an apparatus 100 according to an example embodiment of the invention. The apparatus comprises an elongated apparatus structure 110 and an actuator 120. The actuator 120 is for example a wire made of shape memory material fitted along the length of the elongated apparatus structure. The actuator 120 is configured to change shape of the elongated apparatus structure 110. In FIG. 1 the elongated apparatus structure is shown an unbent position.

Herein it needs to be understood that the shape memory material is only one example of possible actuator. As an alternative, the actuator can comprise a motor or a linear motor accompanied with appropriate mechanisms. —In an example embodiment the actuator comprises a motor with a reduction gear and a ball of wire. The wire is fixed to one end of the elongated strap and the motor with the reduction gear and the ball of wire into the other end. In an example embodiment the actuator comprises a linear motor with a flexible rod. The flexible rod is fixed to one end of the elongated strap and the linear motor with the flexible rod into the other end.

Figure 2:
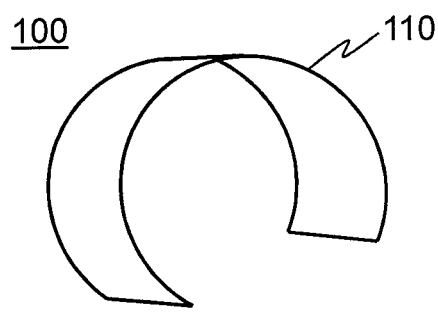
FIG. 2 shows a schematic view of an apparatus according to an example embodiment of the invention in a bent position.

FIG. 2 shows a schematic view of an apparatus 100 according to an example embodiment of the invention in a bent position. The apparatus 100 comprises an elongated apparatus structure 110 bent into a circular form. The circular form suits well for being fitted around a wrist or some other body part of a user. Alternatively the elongated apparatus structure 110 can be configured to take oval or elliptical or some other suitable form.

Figure 3:
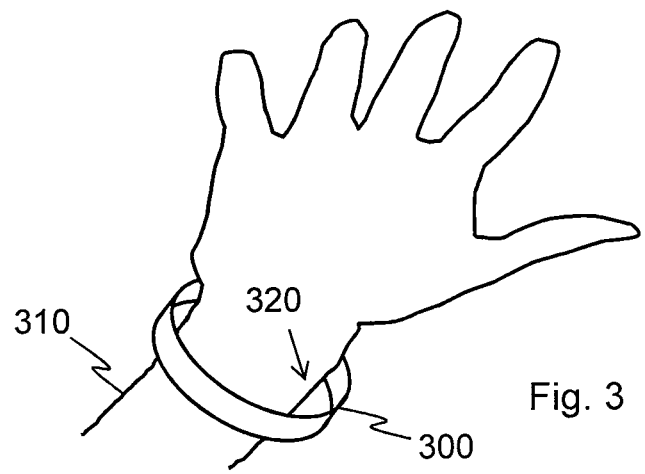
FIG. 3 shows a schematic view of an apparatus according to an example embodiment of the invention in a loosened position.

FIG. 3 shows a schematic view of an apparatus according to an example embodiment of the invention in a loosened or loose fitting position. The apparatus comprises a wrist band 300, which is fitted around user's wrist 310. In the shown loosened position there is a gap 320 formed between user's wrist 310 and the wrist band 300.

Figure 4:
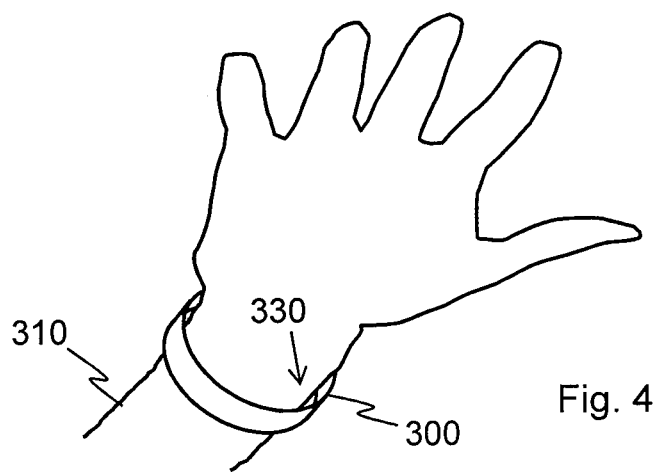
FIG. 4 shows a schematic view of an apparatus according to an example embodiment of the invention in a tightened position.

FIG. 4 shows a schematic view of an apparatus according to an example embodiment of the invention in a tightened or tight fitting position. The apparatus comprises a wrist band 300, which is fitted around user's wrist 310. In the shown tightened position the wrist band 300 is in contact with user's skin or tightened against the user's wrist, i.e. there is minimal gap 330 or no gap at all formed between user's wrist 310 and the wrist band 300.

Figure 5A:
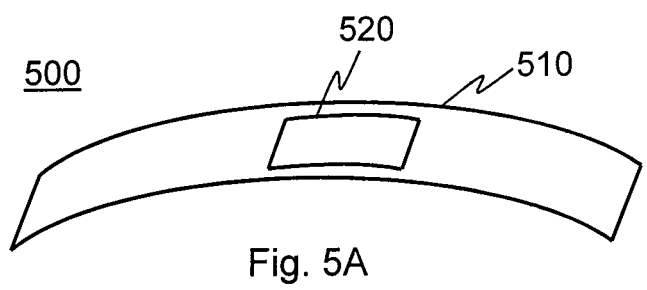
FIG. 5A shows a schematic view of an apparatus according to an example embodiment of the invention.

FIG. 5A shows a schematic view of an apparatus 500 according to an example embodiment of the invention. The apparatus 500 comprises an elongated apparatus structure 510 and a user interface unit 520 on a surface of the elongated apparatus structure 510. The elongated apparatus structure 510 is configured to be fitted around a body part of a user. Further the apparatus 500 comprises an actuator (not shown for the sake of clarity) configured to change shape of the elongated apparatus structure 510.

The user interface unit 520 comprises for example a touch sensitive display. The touch sensitive display comprises for example a touch sensor for detecting the touch of the user. In an example embodiment, the touch sensor comprises a resistive, a surface acoustic wave, a capacitive—such as a surface capacitance, a projected capacitance, a mutual capacitance, or self-capacitance—an infrared, an optical, a dispersive signal and/or acoustic pulse recognition touch sensor or an array thereof. A skilled person appreciates that the user interface unit, in a further example embodiment, comprises further elements such as hardware or soft buttons or further display units. In a further example embodiment, the user interface unit 520 is covered with a glass. It is to be understood that in addition to the user interface unit 520 shown in FIG. 5A the apparatus 500 can comprise other elements, such as a processor or a communication unit.

Figure 5B:
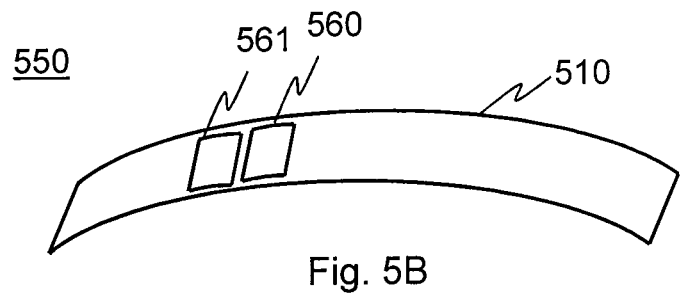
FIG. 5B shows a schematic view of an apparatus according to an example embodiment of the invention.

FIG. 5B shows a schematic view of an apparatus 550 according to an example embodiment of the invention. The apparatus 550 comprises an elongated apparatus structure 510 and two sensors 560 and 561 on a surface of the elongated apparatus structure 510. The sensors are for example sensors configured to measure heart rate, blood pressure, or skin moisture. The elongated apparatus structure 510 is configured to be fitted around a body part of a user. Further the apparatus 550 comprises an actuator (not shown for the sake of clarity) configured to change shape of the elongated apparatus structure 510. In an example embodiment the actuator is configured to change the shape of the elongated apparatus structure so that the elongated apparatus structure is tightened around the body part of the user when the sensors are in operation, i.e. collect data.

Figure 5C:
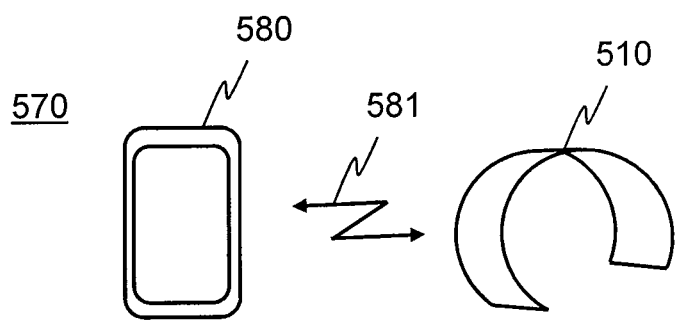
FIG. 5C shows a schematic view of an apparatus according to an example embodiment of the invention.

FIG. 5C shows a schematic view of an apparatus 570 according to an example embodiment of the invention. The apparatus 570 comprises an elongated apparatus structure 510 and an electronic device 580. The elongated apparatus structure 510 is configured to be fitted around a body part of a user. The electronic device 580 and the elongated apparatus structure 510 are configured to communicate with each other over a wireless communication connection 581, such as a Bluetooth connection. Further the apparatus 570 comprises an actuator (not shown for the sake of clarity) configured to change shape of the elongated apparatus structure 510. In an example embodiment the actuator is configured to change the shape of the elongated apparatus structure so that tightness of the elongated apparatus structure 510 around the body part of the user is changed depending on activity in the electronic device 580. In an example embodiment a processor in the electronic device 580 is configured to control the actuator to change the shape of the elongated apparatus structure 510 over the wireless connection 581.

Figure 6:
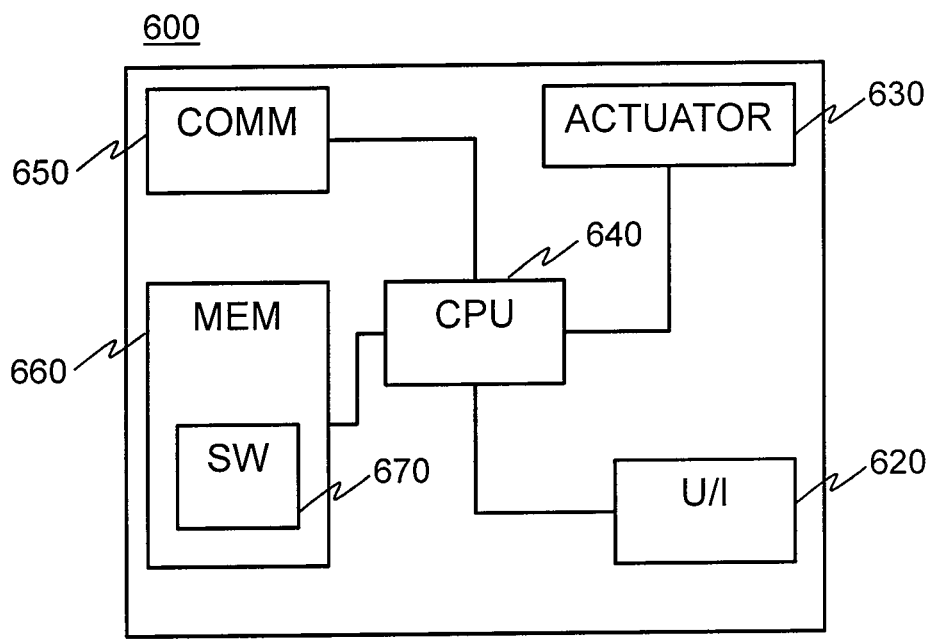
FIG. 6 shows a schematic block diagram of an apparatus according to an example embodiment of the invention.

FIG. 6 shows a schematic block diagram of an apparatus 600 according to an example embodiment of the invention. The apparatus 600 comprises a communication interface module 650, a processor 640 coupled to the communication interface module 650, and a memory 660 coupled to the processor 640. The apparatus further comprises an actuator 630 and a user interface (U/I) unit 620, such as a touch sensitive display, which are coupled to the processor 640. In an example embodiment, the apparatus 600 further comprises one or more sensors configured to measure for example heart rate or skin moisture.

The memory 660 comprises a work memory and a non-volatile memory such as a read-only memory, flash memory, optical or magnetic memory. In the memory 660, typically at least initially in the non-volatile memory, there is stored software 670 operable to be loaded into and executed by the processor 640. The software 670 may comprise one or more software modules and can be in the form of a computer program product that is software stored in a memory medium.

It shall be understood that any coupling in this document refers to functional or operational coupling; there may be intervening components or circuitries in between coupled elements unless expressly otherwise described.

The communication interface module 650 is configured to provide local communications over one or more local links. The links may be wired and/or wireless links. The communication interface 650 may further or alternatively implement telecommunication links suited for establishing links with other users or for data transfer, e.g. using the Internet. Such telecommunication links may be links using any of: wireless local area network links, Bluetooth, ultra-wideband, cellular or satellite communication links. The communication interface 650 may be integrated into the apparatus 600 or into an adapter or card that may be inserted into a suitable slot or port of the apparatus 600. While FIG. 6 shows one communication interface 650, the apparatus may comprise a plurality of communication interfaces 650. In a further example embodiment, the apparatus further 600 comprises a near field communication (NFC) unit.

The processor 640 is, for instance, a central processing unit (CPU), a microprocessor, a digital signal processor (DSP), a graphics processing unit, an application specific integrated circuit (ASIC), a field programmable gate array, a microcontroller or a combination of such elements. FIG. 6 shows one processor 640, but the apparatus 600 may comprise a plurality of processors. In an example embodiment the processor is configured, in response to certain activity in the processor or in the apparatus 600, to control the actuator 630 to change shape of the apparatus 600, and particularly to control the actuator 630 to change tightness of the apparatus 600 around a body part of a user or tightness of a suitable part of the apparatus 600 around a body part of a user.

As mentioned in the foregoing, the memory 660 may comprise volatile and a non-volatile memory, such as a read-only memory (ROM), a programmable read-only memory (PROM), erasable programmable read-only memory (EPROM), a random-access memory (RAM), a flash memory, a data disk, an optical storage, a magnetic storage or a smart card. In some example embodiments, only volatile or non-volatile memory is present in the apparatus 600. Moreover, in some example embodiments, the apparatus comprises a plurality of memories. In some example embodiments, various elements are integrated. For instance, the memory 660 can be constructed as a part of the apparatus 600 or inserted for example into a slot or a port. Further still, the memory 660 may serve the sole purpose of storing data, or it may be constructed as a part of an apparatus serving other purposes, such as processing data. Similar options are thinkable also for various other elements.

A skilled person appreciates that in addition to the elements shown in FIG. 6, the apparatus 600 may comprise other elements, such as microphones, displays, as well as additional circuitry such as a camera unit, further input/output (I/O) circuitries, memory chips, application-specific integrated circuits (ASIC), processing circuitry for specific purposes such as source coding/decoding circuitry, channel coding/decoding circuitry and ciphering/deciphering circuitry. Additionally, the apparatus 600 may comprise a disposable or rechargeable battery (not shown) for powering the apparatus if external power supply is not available.

It is also useful to realize that the term apparatus is used in this document with varying scope. In some of the broader claims and examples, the apparatus may refer to only a subset of the features presented in FIG. 6 or even be implemented without any one of the features of FIG. 6.

The term apparatus may refer to a single physical apparatus or to an apparatus comprising two or more physically separate parts. One needs to understand that elements shown in FIG. 6 for example may be implemented in more than one physically separate parts. There may be for example a wearable part and a separate other part forming the apparatus. Different parts forming the apparatus may communicate with each other over a suitable wireless communication link. For example, the term apparatus may refer to a combination of a wrist band and an electronic device, such as a mobile phone.

Figure 7:
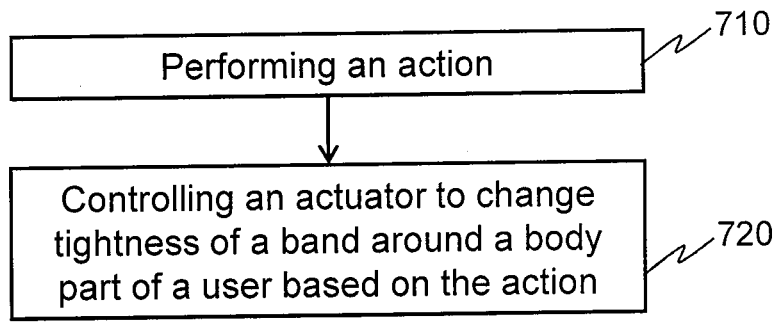
FIG. 7 shows a flow diagram illustrating a method according to an example embodiment of the invention.

FIG. 7 shows a flow diagram illustrating a method according to an example embodiment of the invention. The method may be performed for example by the apparatus 100, 300, 500, 550, 570 or 600 of previous Figures. In phase 710 of the method, the apparatus performs an action, and in phase 720, an actuator is controlled to change tightness of an elongated apparatus structure, such as a band or a strap, around a body part of a user based on the action. Examples of suitable actions include for example: collection of data using one or more sensors, receipt of an incoming call or message, detection of a need to alert the user, and the like. In an example the elongated apparatus structure is a wrist band and the wrist band is tightened or loosened around a wrist of the user based on the action.

In an example embodiment of the invention, the apparatus performing the action is part of the band that is fitted around the body part of the user. In another example, the apparatus performing the action is a separate apparatus that is configured to communicate with a processing unit in the band over a suitable wireless communication connection.

Figure 8:
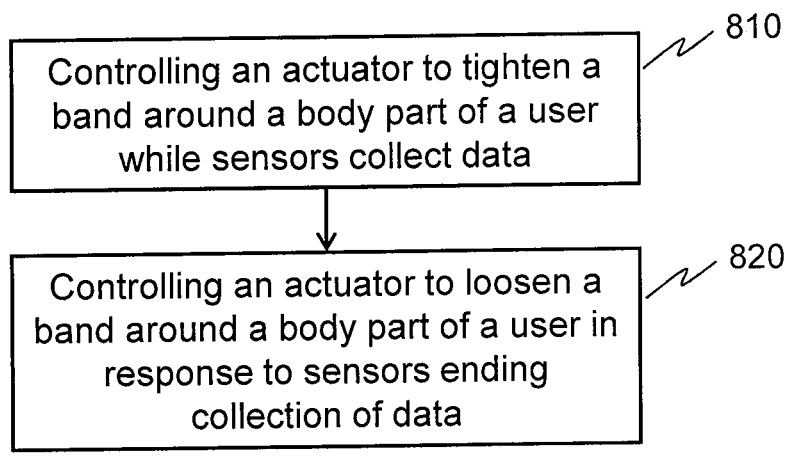
FIG. 8 shows a flow diagram illustrating a method according to an example embodiment of the invention.

FIG. 8 shows a flow diagram illustrating a method according to an example embodiment of the invention. The method may be performed for example by the apparatus 100, 300, 500, 550, 570 or 600 of previous Figures. In this example there are one or more sensors arranged in an elongated apparatus structure, such as a band, that is fitted around a body part of a user. In phase 810 of the method, an actuator is controlled to tighten the band around the body part of the user while the sensors collect data. The band may be tightened for example when the apparatus initiates collection of data through the sensors. In phase 820, the actuator is controlled to loosen the band around the body part of the user in response to the sensors ending collection of data. In an example the elongated apparatus structure is a wrist band and the wrist band is tightened or loosened around a wrist of the user.

For collection of data, e.g. heart rate, blood pressure or skin moisture, through sensors it is advantageous that the sensors are in contact with skin of the user. When the sensors do not collect data there is no need to have a skin contact, though. Use of the band is more pleasant to the user if the band is not at all times tightened around the user's wrist or other body part. Therefore better user experience can be achieved by automatically loosening the band when the sensors end collection of data and by automatically tightening the band for the duration of the sensors collecting data.

For collection of data, e.g. heart rate, blood pressure or skin moisture, through sensors it is advantageous that the pressure with which the sensors are in contact with the skin of the user is reproducible. In an example embodiment one or more of the following mechanisms are included in the band for ensuring that the pressure is the same for all measurements: a pressure sensor configured to detect band's compression force against the skin, a strain-gauge transducer configured to detect curvature of the band, a shape memory alloy actuator configured to detect curvature of the band (the resistance of a shape memory alloy wire changes when the length of the wire changes and this can be used for curvature detection).

Figure 9:
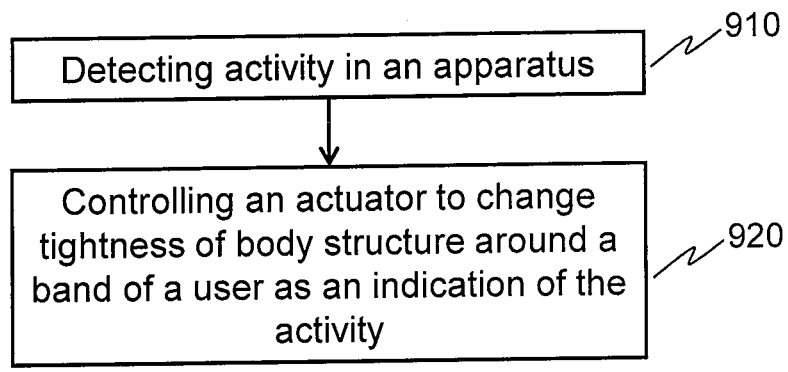
FIG. 9 shows a flow diagram illustrating a method according to an example embodiment of the invention.

FIG. 9 shows a flow diagram illustrating a method according to an example embodiment of the invention. The method may be performed for example by the apparatus 100, 300, 500, 550, 570 or 600 of previous Figures. In phase 910 of the method, activity in an apparatus is detected. For example, it is detected that an incoming call or message is received, or an alert is triggered (such as low battery charging level, reminder in a calendar, availability of new information etc.). In phase 920, an actuator is controlled to change shape of an elongated apparatus structure, such as a band or a strap, in order to change tightness of the elongated apparatus structure around a body part of a user as an indication of the activity. In an example the elongated apparatus structure is a wrist band and the wrist band is tightened or loosened around a wrist of the user as an indication of the activity. In an example the band is periodically tightened and loosened. In this way a new type of user interaction is provided. In an example, the user can be informed of an action without the user needing to look at the device since the user senses the band being tightened around the wrist or other body part.

In this example the apparatus in which the activity is detected can be part of the band that is fitted around the body part of the user. Alternatively, the apparatus in which the activity is detected can be a separate apparatus that is configured to communicate with a processing unit in the band over a suitable wireless communication connection.

Without in any way limiting the scope, interpretation, or application of the claims appearing below, a technical effect of one or more of the example embodiments disclosed herein is to provide that one size band fits all. There may be settings in a memory comprising parameters that define how the band shall fit to a user. There may be for example a setting that defines the pressure with which the band is in contact with the skin of the user and/or a setting that defines certain curvature for the band. When the band is fitted to a new user these settings and appropriate sensors and other mechanisms are used for providing fitting that corresponds to the settings. In an example embodiment these setting are user-adjustable. In an example embodiment one or more of the following mechanisms are included in the band for ensuring that the band fits any user (for controlling bending of the band so that the parameters defined in the settings are met): a pressure sensor configured to detect band's compression force against the skin of the user, a strain-gauge transducer configured to detect curvature of the band, a shape memory alloy actuator configured to detect curvature of the band (the resistance of a shape memory alloy wire changes when the length of the wire changes and this can be used for curvature detection).

Another technical effect of one or more of the example embodiments disclosed herein is improved user experience due to the band being tightened only when sensors collect data. Another technical effect of one or more of the example embodiments disclosed herein is to provide reliable measuring due to the band being tightened with the same force every time. Another technical effect of one or more of the example embodiments disclosed herein is to provide possibility for new type of user interaction. For example, the band can be configured to tighten for an indication of an incoming call or text message or as an indication of some other action taking place. As another example of user interaction, the band can be configured to tighten and loosen in cycle to provide vibrating feedback.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes example embodiments of the invention, these descriptions should not be viewed in a limiting sense. Rather, there are several variations and modifications which may be made without departing from the scope of the present invention as defined in the appended claims.

The invention claimed is:

1. An apparatus comprising:
an elongated apparatus structure configured to fit around a body part of a user;
an actuator configured to change shape of the elongated apparatus structure to tighten or loosen the elongated apparatus structure around the body part of the user; and
a pressure sensor configured to detect compression force of the elongated apparatus structure against skin of the body part of the user;
wherein the actuator is configured to automatically change tightness of the elongated apparatus structure around the body part, to achieve a predefined contact pressure of the apparatus structure against the skin of the body part of the user, in response to the pressure sensor detecting the compression force of the apparatus structure against the skin of the body part of the user.

2. The apparatus of claim 1, further comprising:
a communication unit physically part of the elongated apparatus structure, the communication unit configured to receive wireless signals from a remote device, the wireless signals indicating activity in the remote device;
wherein the actuator is configured to automatically change tightness of the elongated apparatus structure around the body part, in response to the communication unit receiving the wireless signals indicating activity in the remote device.

3. The apparatus of claim 1, further comprising:
a processing unit physically separate from the elongated apparatus structure, the processing unit configured to cause transmission of wireless signals in response to activity in the processing unit;
a communication unit physically part of the elongated apparatus structure, the communication unit configured to receive the wireless signals from the processing unit;
wherein the actuator is configured to automatically change tightness of the elongated apparatus structure around the body part, in response to the communication unit receiving the wireless signals from the processing unit.

4. The apparatus of claim 1, further comprising:
a communication unit configured to receive an indication of an incoming wireless signal;

wherein the actuator is configured to automatically change tightness of the elongated apparatus structure around the body part, in response to the communication unit indicating receipt of an indication of an incoming wireless signal.

5. The apparatus of claim 1, further comprising:
a communication unit configured to receive an incoming wireless signal;
wherein the actuator is configured to automatically tighten the elongated apparatus structure around the body part of the user in response to initiating receipt of a wireless signal by the communication unit and automatically loosen the elongated apparatus structure around the body part of the user in response to ending the receipt of the wireless signal by the communication unit.

6. The apparatus of claim 1, further comprising:
a second sensor configured to detect body signal data related to at least one of heart rate, skin moisture, or blood pressure of the user;
wherein the actuator is configured to automatically tighten the elongated apparatus structure around the body part of the user in response to initiating receipt of body signal data of the user by the second sensor and automatically loosen the elongated apparatus structure around the body part of the user in response to ending the receipt of body signal data of the user by the second sensor.

7. The apparatus of claim 1, further comprising:
a memory configured to store parameters specifying the predefined contact pressure of the apparatus structure against the skin of the body part of the user;
wherein the memory is configured to store changes in the parameters when the elongated apparatus structure is fitted to a different user, to establish a fitting that corresponds to the settings.

8. The apparatus of claim 1, further comprising:
a memory configured to store parameters specifying the predefined contact pressure of the apparatus structure against the skin of the body part of the user; and
a processing unit coupled to the actuator, the pressure sensor, and the memory, the processing unit configured to control the actuator to automatically change tightness of the elongated apparatus structure around the body part, to achieve the predefined contact pressure of the apparatus structure against the skin of the body part of the user, in response to the pressure sensor detecting the compression force of the apparatus structure against the skin of the body part of the user.

9. A method comprising:
controlling an apparatus comprising a pressure sensor, an elongated apparatus structure configured to fit around a body part of a user, and an actuator configured to change shape of the elongated apparatus structure; and
controlling the actuator to automatically change tightness of the elongated apparatus structure around the body part, to achieve a predefined contact pressure of the apparatus structure against skin of the body part of the user, in response to the pressure sensor detecting a compression force of the apparatus structure against the skin of the body part of the user.

10. The method of claim 9, further comprising:
receiving at a communication unit physically part of the elongated apparatus structure, wireless signals from a remote device, the wireless signals indicating activity in the remote device; and
controlling the actuator to automatically change tightness of the elongated apparatus structure around the body part, in response to the communication unit receiving the wireless signals indicating activity in the remote device.

11. The method of claim 9, further comprising:
receiving at a communication unit physically part of the elongated apparatus structure, wireless signals from a processing unit physically separate from the elongated apparatus structure, the wireless signals indicating activity in the processing unit; and
controlling the actuator to automatically change tightness of the elongated apparatus structure around the body part, in response to the communication unit receiving the wireless signals indicating activity in the processing unit.

12. The method of claim 9, further comprising:
receiving an indication of an incoming wireless signal at a communication unit of the apparatus; and
controlling the actuator to automatically change tightness of the elongated apparatus structure around the body part, in response to the communication unit indicating receipt of an indication of an incoming wireless signal.

13. The method of claim 9, further comprising:
receiving an incoming wireless signal at a communication unit of the apparatus; and;
controlling the actuator to automatically tighten the elongated apparatus structure around the body part of the user in response to initiating receipt of a wireless signal by the communication unit and automatically loosen the elongated apparatus structure around the body part of the user in response to ending the receipt of a wireless signal by the communication unit.

14. The method of claim 9, further comprising:
detecting body signal data with a second sensor in the apparatus, the body signal data related to at least one of heart rate, skin moisture, or blood pressure of the user;
controlling the actuator to automatically tighten the elongated apparatus structure around the body part of the user in response to initiating receipt of body signal data of the user by the second sensor and automatically loosen the elongated apparatus structure around the body part of the user in response to ending the receipt of body signal data of the user by the second sensor.

15. The method of claim 9, further comprising:
storing parameters in a memory of the apparatus, the parameters specifying the predefined contact pressure of the apparatus structure against the skin of the body part of the user; and
controlling the memory to store changes in the parameters when the elongated apparatus structure is fitted to a different user, to establish a fitting that corresponds to the settings.

16. An apparatus comprising:
an elongated apparatus structure configured to fit around a body part of a user;
an actuator configured to change shape of the elongated apparatus structure to tighten or loosen the elongated apparatus structure around the body part of the user; and
a sensor positioned by the elongated apparatus structure proximate to the body part of the user, the sensor configured to detect body signal data related to at least one of heart rate, perspiration, or blood pressure of the user;
wherein the actuator is configured to automatically change tightness of the elongated apparatus structure around the body part of the user, in response to receipt by the sensor of body signal data of the user related to at least one of heart rate, perspiration, or blood pressure of the user.

17. The apparatus of claim 16, wherein the actuator further comprises:
a wire having one end connected to the elongated apparatus structure; and
a motor with a reduction gear configured to pull on an opposite end of the wire to change tightness of the elongated apparatus structure around the body part.

18. The apparatus of claim 16, further comprising:
a communication unit physically part of the elongated apparatus structure, the communication unit configured to receive wireless signals from a remote device, the wireless signals indicating activity in the remote device;
wherein the actuator is configured to automatically change tightness of the elongated apparatus structure around the body part, in response to the communication unit receiving the wireless signals indicating activity in the remote device.

19. An apparatus comprising:
an elongated apparatus structure configured to fit around a body part of a user;
an actuator configured to change shape of the elongated apparatus structure to tighten or loosen the elongated apparatus structure around the body part of the user; and
a pressure sensor configured to detect compression force of the elongated apparatus structure against the body part of the user;
a second sensor positioned by the elongated apparatus structure proximate to the body part of the user, the second sensor configured to detect body signal data related to at least one of heart rate, perspiration, or blood pressure of the user;
wherein the actuator is configured to automatically change tightness of the elongated apparatus structure around the body part, in response to the pressure sensor detecting the compression force of the apparatus structure against the body part of the user; and
wherein the actuator is configured to automatically change tightness of the elongated apparatus structure around the body part of the user, in response to receipt by the second sensor of body signal data of the user related to at least one of heart rate, perspiration, or blood pressure of the user.

20. The apparatus of claim 19, wherein the actuator further comprises:
a wire having one end connected to the elongated apparatus structure; and
a motor with a reduction gear configured to pull on an opposite end of the wire to change tightness of the elongated apparatus structure around the body part.

21. The apparatus of claim 20, further comprising:
a communication unit physically part of the elongated apparatus structure, the communication unit configured to receive wireless signals from a remote device, the wireless signals indicating activity in the remote device;
wherein the actuator is configured to automatically change tightness of the elongated apparatus structure around the body part, in response to the communication unit receiving the wireless signals indicating activity in the remote device.

22. A method comprising:
controlling an apparatus comprising a sensor, an elongated apparatus structure configured to fit around a body part of a user, and an actuator configured to change shape of the elongated apparatus structure, the sensor positioned by the elongated apparatus structure proximate to the body part of the user, the sensor configured to detect body signal data related to at least one of heart rate, perspiration or blood pressure of the user; and
controlling the actuator to automatically change tightness of the elongated apparatus structure around the body part, in response to receipt by the sensor of body signal data of the user related to at least one of heart rate, perspiration, or blood pressure of the user.

23. The method of claim 22, further comprising:
controlling the actuator to automatically change tightness of the elongated apparatus structure around the body part, in response to a pressure sensor detecting a compression force of the apparatus structure against the body part of the user, the pressure sensor positioned by the elongated apparatus structure proximate to the body part of the user and configured to detect compression force of the elongated apparatus structure against the body part of the user.

24. The method of claim 22, further comprising:
receiving at a communication unit physically part of the elongated apparatus structure, wireless signals from a remote device, the wireless signals indicating activity in the remote device; and
controlling the actuator to automatically change tightness of the elongated apparatus structure around the body part, in response to the communication unit receiving the wireless signals indicating activity in the remote device.

* * * * *